United States Patent [19]

Enomoto

[11] Patent Number: 5,221,614
[45] Date of Patent: * Jun. 22, 1993

[54] METHOD AND REAGENT FOR DETERMINING THE BIOLOGICAL ACTIVITY OF ANTITHROMBIN III BY MEASURING COAGULATION TIME

[75] Inventor: Masayasu Enomoto, Takatsuki, Japan

[73] Assignee: Nippon Shoji Kabushiki Kaisha, Osaka, Japan

[*] Notice: The portion of the term of this patent subsequent to Mar. 3, 2009 has been disclaimed.

[21] Appl. No.: 782,122

[22] Filed: Oct. 25, 1991

Related U.S. Application Data

[62] Division of Ser. No. 432,726, filed as PCT/JP89/00173 on Feb. 22, 1989, Pat. No. 5,093,237.

[30] Foreign Application Priority Data

Mar. 3, 1988 [JP] Japan ............... 63-052295

[51] Int. Cl.⁵ .................................. C12Q 1/00
[52] U.S. Cl. .......................... 435/13; 436/18; 436/69; 530/381; 530/393
[58] Field of Search ............ 436/18, 69, 175; 435/13; 530/393, 381, 384

[56] References Cited

U.S. PATENT DOCUMENTS

| | | | |
|---|---|---|---|
| 4,106,990 | 8/1978 | Karges et al. | 435/13 |
| 4,139,415 | 2/1979 | Yin et al. | 435/13 |
| 4,409,327 | 10/1983 | Bartl et al. | 435/13 |
| 4,948,724 | 8/1990 | Yin | 436/69 |
| 5,093,237 | 3/1992 | Enomoto | 436/69 |

FOREIGN PATENT DOCUMENTS 58-220697 12/1983 Japan.
62-159048 7/1987 Japan.

OTHER PUBLICATIONS

Dornheim, Dialog Abstract of DD250711 (Oct. 21, 1987), WPI Acc. No. 88-071405/11.
Nippon, Dialog Abstract of JP580/0522 (Jan. 21, 1983), WIP Acc. No. 83-730870/32.
Nippon, Dialog Abstract of JP60048930 (Mar. 16 1985), WPI Acc. No. 85-102739/17.

Primary Examiner—Michael G. Wityshyn
Assistant Examiner—William H. Beisner
Attorney, Agent, or Firm—Wegner, Cantor, Mueller & Player

[57] ABSTRACT

A method for determination of biological activity of AT III which comprises mixing a specimen, AT III free-extrinsic coagulation factor-containing plasma, heparin and a prothrombin time-measuring reagent or a factor X-activating reagent and then measuring a coagulation time, and a reagent and plasma to be used therefor.

4 Claims, 2 Drawing Sheets

METHOD AND REAGENT FOR DETERMINING THE BIOLOGICAL ACTIVITY OF ANTITHROMBIN III BY MEASURING COAGULATION TIME

This application is a continuation of Ser. No. 07/432,726, filed as PCT/JP89/00173 on Feb. 22, 1989, now U.S. Pat. No. 5,093,237.

FIELD OF THE INVENTION

The present invention relates to a method for determination of biological activity of antithrombin III (hereinafter abbreviated as AT III) in plasma and a reagent therefor.

BACKGROUND OF THE INVENTION

AT III is a serine protease inhibitor present in blood in a large amount (from 20 to 30 mg/dl) and is known as a coagulation inhibitor. As described hereinafter, the blood coagulation reaction includes an intrinsic coagulation reaction pathway and an extrinsic coagulation reaction pathway. Various coagulation factors take part in respective pathways and AT III inhibits most of the activated coagulation factors. Particularly, as the action of AT III, the inhibition of thrombin, which is activated factor II (IIa), and activated factor X (Xa) is considered to be of importance. And, since the reaction of coagulation factors is inhibited more effectively at an early stage in the blood coagulation system, AT III is considered to play a particularly important role in the inhibition of factor Xa which takes part in a stage earlier than factor IIa.

Clinically, attention is directed to AT III in AT III production depressed conditions such as hepatocirrhosis and undernutrition, AT III consuming conditions such as disseminated intravascular coagulation (DIC) and other progressive coagulation conditions, conditions wherein AT III is lost into urine such as nephrosis syndrome, congenital AT III deficiency disease and the like. Therefore, for diagnosis of these conditions, it has been requested to establish a precise, rapid and easy method for determination of biological activity of AT III.

Hitherto, as a method for determination of biological activity of AT III, there have been known a method using a synthetic substrate and a method utilizing coagulation activity. Among them, the method using synthetic substrate is carried out by adding a synthetic substrate and an excess amount of factor IIa to a specimen plasma and measuring anti-IIa activity of AT III in the specimen. This method is excellent because the determination can be carried out within a short period of time. However, the method has many problems, for example, the method has different specificity depending upon the kind of synthetic substrates and a synthetic substrate is very expensive. Further, factor IIa to be used is less stable and, since IIa factor is apt to be adsorbed by glass, a plastic cell should be used in the measurement. Furthermore, since the method requires measuring apparatuses such as a spectrophotometer and a fluorophotometer, the economical burden becomes large.

On the other hand, in the coagulation method, a concentration of AT III is determined by subjecting a specimen plasma to heat treatment to remove fibrinogen, adding an excess amount of factor IIa and measuring a coagulation time due to conversion of fibrinogen to fibrin to obtain the anti-IIa activity of AT III in the specimen. However, these operations of this method are complicated and the determination takes a long period of time, for example, not less than one hour.

OBJECTS OF THE INVENTION

Under these circumstances, the present inventor has studied intensively in order to establish a precise, rapid and easy method for determination of AT III without the above problems. As a result, the present inventor has found that this objective can be attained by a novel method for determination of AT III wherein a coagulation method is employed by utilizing the extrinsic coagulation reaction pathway of the blood coagulation reaction and using AT III deficient plasma wherein AT III has been removed.

Measurement of coagulation factor activity using a factor deficient plasma wherein a desired factor has been removed is utilized in the determination of various blood coagulation factors [for example, Kensa to Gijutsu, Vol. 13, No. 7, pages 611 to 616 (July, 1985)]. In addition, the use of protein S deficient plasma is proposed for determination of biological activity of protein S which is one of blood coagulation inhibitors (Japanese Patent Laid Open Publication No. 62-159048).

However, a blood coagulation factor has the reverse activity relative to a coagulation inhibitor such as AT III and measurement thereof is substantially different from that of a coagulation inhibitor. In addition, although protein S is a coagulation inhibitor, it acts as a cofactor of activated protein C and, therefore, its action is substantially different from that of AT III. Further, the above proposed method utilizes the intrinsic coagulation reaction pathway of the blood coagulation reaction. Thus, in view of this, the above proposed method is also substantially different from the method of the present invention. Furthermore, since AT III is contained in plasma in a large amount and specific removal thereof is difficult, use of AT III deficient plasma has not been known heretofore in the prior art.

SUMMARY OF THE INVENTION

The present invention provides AT III free-extrinsic coagulation factor-containing plasma wherein AT III has been specifically removed but extrinsic coagulation factors are contained. The present invention also provides a method for determination of biological activity of AT III which comprises mixing a specimen, AT III free-extrinsic coagulation factor-containing plasma, heparin and a prothrombin time measuring reagent or a factor X-activating reagent and then measuring coagulation time. The present invention further provides a reagent for determination of biological activity of AT III which comprises AT III free-extrinsic coagulation factor-containing plasma, heparin and a prothrombin time-measuring reagent or a factor X-activating reagent.

DETAILED DESCRIPTION OF THE INVENTION

Figure 1:
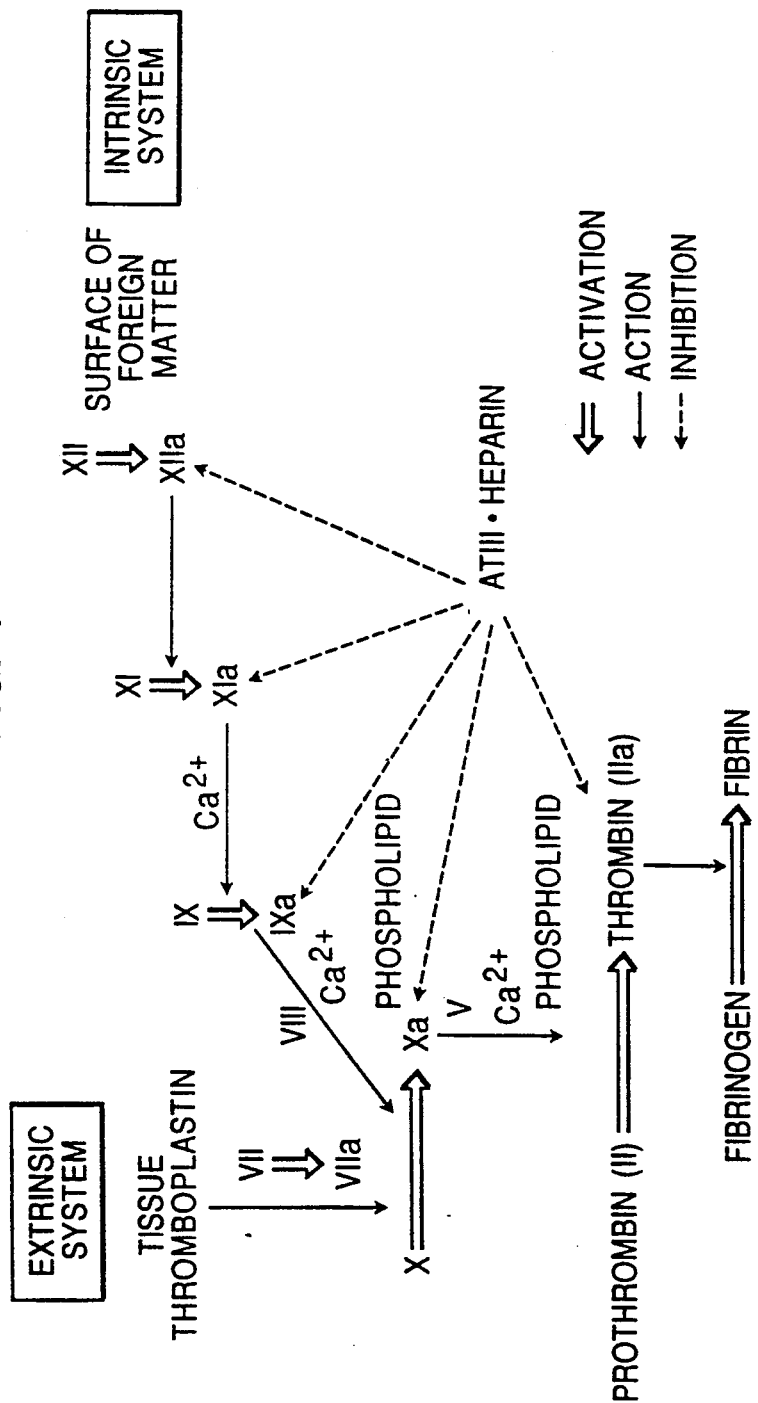
FIG. 1 is a schematic diagram illustrating the blood coagulation reaction system and the action of AT III.

As shown in accompanying FIG. 1, in the blood coagulation reaction, there are the intrinsic coagulation reaction pathway where coagulation is started by contact with the surface of a foreign matter and the extrinsic coagulation reaction pathway where reaction is started by tissue thromoboplastin. Among them, the intrinsic coagulation reaction pathway is considered to be apt to produce many errors because many reactions are involved. Therefore, in the present invention, the extrinsic coagulation reaction is utilized. That is, the present invention utilizes a reaction wherein the coagulation reaction is started by tissue thromboplastin and precipitation of fibrin is caused through actions of factor VII, activated factor VII (VIIa), factor X, activated factor X (Xa), factor V, factor II, activated factor II (IIa) and fibrinogen or, in the case of using a factor X-activating reagent, through actions of factor X and the subsequent factors. In this pathway, AT III inhibits factors IIa and Xa in the presence of heparin. According to the present invention, biological activity of AT III in a specimen is obtained in terms of delay in a blood coagulation time by using only simple conventional apparatuses for measuring blood coagulation time and more precise measurement of biological activity of AT III can be carried out.

The specimen to which the method of the present invention is applicable is usually plasma. According to a conventional method, blood is collected from a subject to be tested and plasma is separated from it.

The AT III free-extrinsic coagulation factor-containing plasma to be used means a plasma from which AT III has been removed specifically and which contains the extrinsic coagulation factors, factor VII, factor X, factor V, factor II and fibrinogen. When the prothrombin times of the plasma are measured in the presence of 5 to 20 U/ml of heparin and in the absence of heparin, the difference thereof should be within 10 seconds, preferably 5 seconds. When a factor X-activating reagent is used, factor VII may not be contained. Hitherto, for example, Douglas M. Tollefsen et al., Journal of Biological Chemistry, Vol. 257, No. 5, pages 2162 to 2169 (March, 1982) discloses treatment of plasma by heparin-affinity chromatography as one step of separation and purification of heparin cofactor II. However, the protein content of the product thus treated is only about 1/300 of that of the original plasma and the product can hardly be said to be plasma. To the contrary, according to the present invention, it has been found that AT III can be specifically adsorbed without substantial adsorption of extrinsic coagulation factors by adding a salt to plasma so that the salt content attains a certain concentration and subjecting to heparin-affinity chromatography equilibrated with the same concentration of the salt to give AT III free-extrinsic coagulation factor-containing plasma which has not been obtained heretofore in the prior art. Namely, although coagulation (prothrombin time) did not take place when heparin was added in a concentration of 12 U/ml to plasma before subjecting to chromatography, the fraction which was not adsorbed by heparin-affinity chromatography showed almost the same coagulation time as that of the original plasma to which no heparin was added. From this, it was recognized that AT III free-extrinsic coagulation factor-containing plasma can be obtained by heparin-affinity chromatography. Desirably, heparin-affinity chromatography is carried out by using a solution of 0.05 to 0.7M, preferably, 0.1 to 0.3M of a salt such as sodium chloride or potassium chloride in a buffer, for example, Michaelis buffer, phosphate buffer, Tris-HCl buffer or the like, preferably, that of 10 to 50 mM and pH 7.0 to 7.5 and a carrier such as heparin-agarose, heparin-sepharose or the like. The salt is also added to plasma to be chromatographed in the same concentration. Thus, in the present invention, AT III free-extrinsic coagulation factor-containing plasma can be obtained. The plasma can be also obtained by an antigen-antibody reaction. That is, the desired plasma can be obtained by immunoprecipitation or immunoaffinity chromatography using anti-AT III antibody obtained by immunizing goat, rabbit, mouse or the like with AT III as an antigen or anti-AT III monoclonal antibody obtained by conventional cell fusion technique or the like to specifically remove AT III from plasma.

The prothrombin time-measuring reagent comprises tissue thromboplastin derived from internal organs such as brain, lung, placenta and the like of human being, rabbit and the like, and calcium. And, the factor X-activating reagent comprises a protease which activates factor X specifically, for example, Russell's viper venom, cephalin and calcium. Including heparin, all these reagents are commercially available. For example, as Russell's viper venom, there is Stypven of Wellcome Company, England. As a reagent containing Russell's viper venom and cephalin, there is Stypven-cephalin reagent included in a factor X determination kit of Bio Mérieux S.A., France. In the present invention, they can be used.

In general, determination of biological activity of AT III according to the present invention can be carried out by mixing a predetermined amount of specimen plasma or its diluted solution and AT III free-extrinsic coagulation factor-containing plasma, incubating the mixture at 25° to 45° C., usually, 37° C. for 1 to 10 minutes, preferably 2 to 5 minutes, adding a prothrombin time-measuring reagent containing heparin or a factor X activating reagent and then measuring coagulation time at the same temperature. Separately, plasma of a healthy subject is diluted in various concentrations and, according to the same manner, coagulation times are measured. The coagulation times are plotted relative to the degrees of dilution to obtain a calibration curve. From the calibration curve thus obtained, the ratio of AT III activity of the specimen to that of the healthy subject is obtained and the result is expressed by this ratio.

Usually, specimen plasm is diluted with a buffer at pH 6.0 to 8.5, for example, Michaelis buffer, Tris-HCl buffer, phosphate buffer, oren-veronal buffer, imidazole buffer or Good's buffer such as HEPES, TES or MOPS and, preferably, 5 to 100 μl of specimen plasma or a diluted solution thereof is admixed with 100 μl of AT III free-extrinsic coagulation factor-containing plasma.

Although concentration of respective reagents can be selected appropriately, desirably, the concentration of heparin is 0.1 to 50000 U/ml, preferably, 1 to 50 U/ml (the unit of heparin was determined according to "heparin sodium authentic sample and method for determination thereof" in the Japanese Pharmacopoeia), the concentration of thromboplastin in a prothrombin time-measuring reagent is 0.001 to 15 mg/ml, preferably, 0.01 to 0.1 mg/ml and the concentration of calcium is 2 to 500 mM, preferably, 5 to 50 mM. Further, desirably, the concentration of factor X activating protease in a factor X-activating reagent, for example, the concentration of Russell's viper venom is such that the activity thereof is corresponding to a coagulation time of within the range of 5 to 200 seconds, preferably, 10 to 50 seconds in a coagulation test using normal plasma, the concentration of cephalin is from 0.01 µg to 5 mg/ml, preferably, 1 µg to 200 µg/ml and, as described above, the concentration of calcium is 2 to 500 mM, preferably, 5 to 50 mM. In general, a prothrombin time-measuring reagent or a factor X-activating reagent containing heparin is used in a proportion of 50 to 300 µl per 100 µl of AT III free-extrinsic coagulation factor-containing plasma.

Thus, according to the method of the present invention, biological activity of AT III can be determined precisely, rapidly and easily and it has been found that the data have a high correlation with those obtained by the conventional method using synthetic substrate.

The reagent for determination of biological activity of AT III of the present invention comprises the above AT III free-extrinsic coagulation factor-containing plasma and the above respective reagents. Usually, AT III free-extrinsic coagulation factor-containing plasma is in a lyophilized form prepared according to the conventional method and is reconstituted with purified water or a buffer upon use. Further, the respective reagents can be in the form of a solution obtained according to the conventional method wherein all the reagents, optionally together with an excipient are dissolved in purified water or a buffer so that the predetermined concentrations of respective reagents can be obtained in a reaction system and thereby the solution can be directly used in the determination as it is. Or, they can be in the form of a concentrated solution which can be appropriately diluted to a desired concentration, or in a lyophilized form. Further, respective reagents can be prepared in the form of a solution, a lyophilized product or the like, individually. The determination reagent of the present invention is used as a so-called reagent kit by combining these reagents.

The following Examples further illustrate the present invention in detail.

EXAMPLE 1

Preparation of AT III Free-Extrinsic Coagulation Factor-Containing Plasma

About 20 ml of heparin-agarose (type II) (manufactured by Sigma Company, U.S.A.) was packed in a cylinder of a plastic injector and was equilibrated with 20 mM Tris buffer (pH 7.3) containing 0.1M of sodium chloride and 0.35% of sodium citrate.

Separately, human plasma (negative relative to HBsAg and HIV antibody, obtained from Plasma Biological Service Incorporated, U.S.A.) was centrifuged at 2500 rpm for 10 minutes, the precipitate was removed, and 1.8 ml of 2M sodium chloride was added to 36 ml of plasma. The plasma to which sodium chloride had been added was passed through the column and the fraction which was not adsorbed was recovered in plastic cups in 2 ml portions.

By the way, column operation was carried out at room temperature and plasma and respective fractions were stored in ice.

The prothrombin time of the recovered plasma was measured in the presence of 12 U/ml of heparin or in the absence of heparin by using Thrombomat (rabbit brain tissue thromboplastin manufactured by Bio Mérieux S.A., France). The results are shown in Table 1.

TABLE 1

| Fraction No. | In the absence of heparin (sec.) | In the presence of heparin (sec.) |
|---|---|---|
| 1 | >250 | — |
| 2 | >250 | — |
| 3 | 28.9 | 45.8 |
| 4 | 16.6 | 19.0 |
| 5 | 15.0 | 17.0 |
| 6 | 14.2 | 15.7 |
| 7 | 13.8 | 15.6 |
| 8 | — | 15.3 |
| 9 | — | 14.8 |
| 10 | — | 14.7 |
| 11 | 14.0 | 14.7 |
| 12 | 13.8 | 14.7 |
| 13 | 13.9 | 14.5 |
| 14 | 14.6 | 15.3 |
| 15 | 17.2 | 19.0 |
| 16 | 23.1 | 26.7 |
| 17 | 28.8 | 33.8 |
| 18 | 47.0 | 48.0 |
| Starting plasma | 15.2 | >250 |

—: not measured

As seen from Table 1, plasma before subjecting to the column coagulated in 15.2 seconds in the absence of heparin and did not coagulate within 250 seconds in the presence of heparin. To the contrary, in the case of the fraction which was not adsorbed, for example, Fraction No. 11, it coagulated in 14.0 seconds in the absence of heparin and 14.7 seconds in the presence of heparin. From these results, it was judged that, AT III in plasma of Fraction Nos. 4 to 15 was almost completely removed and the extrinsic coagulation factors, i.e., factor VII, factor X, factor V, factor II and fibrinogen were contained.

Then, Fraction Nos. 4 to 15 were combined to obtain AT III free-extrinsic coagulation factor-containing plasma and stored at −30° C.

In this Example, about 26 ml of AT III free-entrinsic coagulation factor-containing plasma (hereinafter merely referred to as AT III free plasma) was obtained from 36 ml of plasma.

EXAMPLE 2

(1) Preparation of a Calibration Curve

5 Plasma specimens of healthy subjects were mixed and diluted 5 times with Michaelis buffer (pH 7.35) and this was diluted in 5 steps to obtain 5 specimens. 50 µl of each specimen was admixed with 100 µl of AT III free plasma obtained in Example 1 and warmed at 37° C. for 2 minutes. To this was added 200 µl of an aqueous solution of 0.04 mg/ml of rabbit brain tissue thromboplastin (a solution prepared by dissolving 1 vial of Thrombomat for 10 ml used in Example 1 in 100 ml of a solution containing 5 U/ml of heparin and 25 mM of calcium chloride) warmed to 37° C. or 200 µl of an aqueous solution of Russell's viper venom having coagulation activity of about 20 seconds (a solution prepared by dissolving 1 vial of Stypven-cepharin reagent (manufactured by Bio Mérieux S.A., France) in 2 ml of a solution containing 5 U/ml of heparin and 25 mM of calcium chloride) warmed to 37° C. and the coagulation time was measured.

Figure 2:
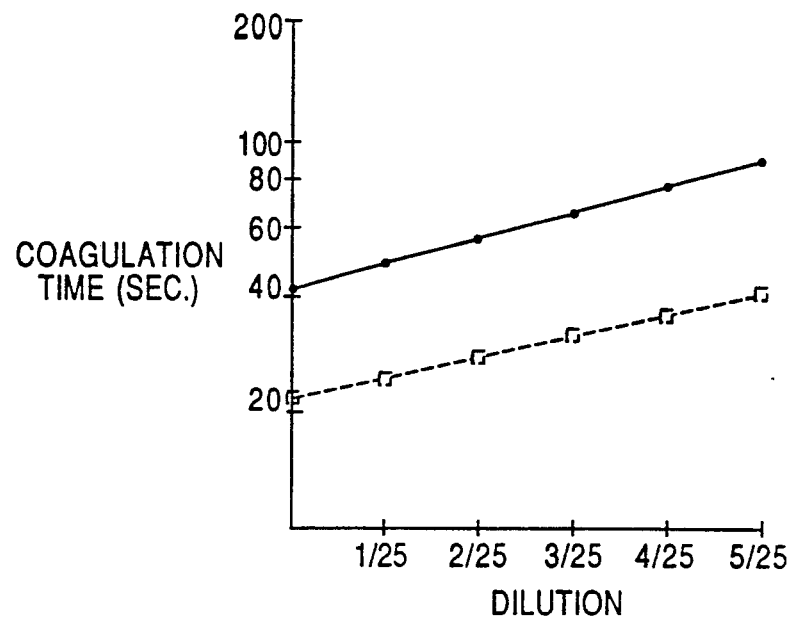
FIG. 2 is a graph illustrating an example of a calibration curve for determination of biological activity of AT III.

When the data were plotted on a semilogarithmic graph paper by taking the degree of dilution of the specimen plasma as x-axis and the coagulation time as y-axis to obtain the linear relationship as shown in the accompanying FIG. 2, the delay in the coagulation time was recognized depending upon the concentration of AT III in plasma.

As seen from FIG. 2, the good linear relationship is obtained between about 42 to 92 seconds in the case of using rabbit brain tissue thromboplastin and between about 22 to 41 seconds in the case of using Russell's viper venom. Thus, it can be used as a calibration curve.

Figure 3:
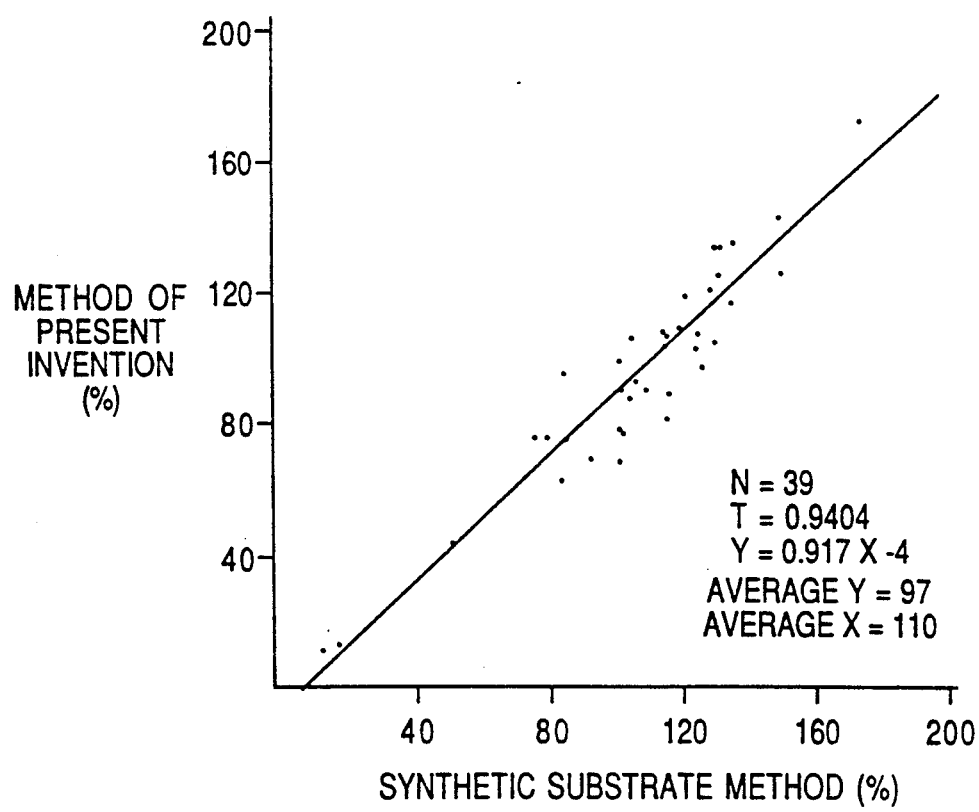
FIG. 3 is a graph illustrating the correlation between the method of the present invention and a known method using a synthetic substrate.

By the way, for comparison, the same specimen was subjected to determination by using a kit for measuring AT III with a synthetic substrate (AT III test "BMY" sold by Boehringer Mannheim Yamanouchi K.K.) and the results were compared with those of the present invention using rabbit brain tissue thromboplastin to examine the correlation. The results are shown in FIG. 3. In FIG. 3, the ordinate corresponds to the data obtained by the method of the present invention and the abscissa corresponds to the data obtained by using BMY. The results are expressed by taking AT III activity % of non-diluted plasma obtained by mixing 5 specimens as 100%.

As seen from FIG. 3, the coefficient of correlation between both methods is high such as 0.940, which shows that the method of the present invention is useful.

(2) Determination

5 Plasma specimens of healthy subjects were diluted 10 times with Michaelis buffer (pH 7.35), respectively. According to the same manner as Example 2 (1), coagulation times were measured by using rabbit brain tissue thromboplastin and AT III activity %'s (AT III activity of non-diluted plasma obtained by mixing 5 specimens was taken as 100%) of each specimen was obtained by using the calibration curve in Example 2 (1). The results are shown in Table 2.

TABLE 2

| Specimen | A | B | C | D | E |
|---|---|---|---|---|---|
| AT III activity % | 103 | 106 | 98 | 96 | 109 |

As shown in Table 2, AT III activity %'s of these plasma specimens of healthy subjects were 96 to 109% and within a normal range of AT III (81 to 118%, Minoru UKITA, Rinsho Byori, special edition No. 70, pages 173 to 180 (1987)).

EXAMPLE 3

Reagent for Determination of Biological Activity of AT III 1 ml each of AT III free plasma obtained in Example 1 was poured into vials and lyophilized according to the conventional method.

Separately, 1 ml each of a solution containing 0.4 mg/ml of rabbit brain tissue thromboplastin (Thrombomat), 50 U/ml (193.4 U/mg) of heparin sodium and 10 mg/ml of sorbitol in purified water was poured into vials and lyophilized according to the conventional method. Both vials were combined to obtain a reagent kit. Upon use, AT III free plasma is dissolved by adding 1 ml of purified water. The thromboplastin reagent is dissolved with 10 ml of a 25 mM calcium chloride solution.

According to the present invention, biological activity of AT III in plasma can be determined easily, rapidly and precisely with a conventional apparatus for measuring the blood coagulation time. Therefore, the present invention can make a great contribution toward clinical diagnosis.

What is claimed is:

1. A method for determination of biological activity of antithrombin III (ATIII) in a specimen of blood from a patient by measuring blood coagulation time, comprising:

mixing a specimen of blood from a patient with ATIII-free, extrinsic coagulation factor-containing plasma;

incubating the mixture;

adding heparin and a prothrombin time-measuring reagent or a factor X activating reagent;

measuring coagulation time of the mixture; and determining ATIII activity of the specimen from the coagulation time.

2. A method for determination of biological activity of antithrombin III (ATIII) in a specimen of blood from a patient by measuring blood coagulation time, comprising:

mixing a specimen of blood from a patient with ATIII-free, extrinsic coagulation factor-containing plasma;

incubating the mixture;

adding heparin and a prothrombin time-measuring reagent or a factor X activating reagent;

measuring coagulation time of the mixture; and determining ATIII activity of the specimen from the coagulation time by using coagulation times for standardization samples which contain normal amounts of AT III with normal biological activity.

3. The method of claim 2, wherein the incubating step is conducted at 25° to 45° C.

4. A reagent for determination of biological activity of antithrombin III (ATIII) which comprises ATIII-free, extrinsic coagulation factor-containing plasma, heparin and a prothrombin time-measuring reagent or a factor X-activating reagent, the extrinsic coagulation factors contained in said plasma being factor VII, factor X, factor V, factor II, and fibrinogen, and the factor X-activating reagent comprising a protease, cephalin and calcium.

* * * * *